United States Patent [19]

Shinohara et al.

[11] Patent Number: 5,264,601

[45] Date of Patent: Nov. 23, 1993

[54] N,O-BIS(TRIMETHYLSILYL) ACETAMIDE STABILIZATION

[75] Inventors: Toshio Shinohara, Takasaki; Muneo Kudo; Susumu Ueno, both of Annaka; Masao Maruyama, Gunma, all of Japan

[73] Assignee: Shin-Etsu Chemical Co., Ltd., Tokyo, Japan

[21] Appl. No.: 921,250

[22] Filed: Jul. 29, 1992

[30] Foreign Application Priority Data

Jul. 31, 1991 [JP] Japan ................................ 3-214674

[51] Int. Cl.⁵ ............................................. C07F 7/10
[52] U.S. Cl. ...................................... 556/401; 548/174
[58] Field of Search ................. 556/401; 548/168, 169

[56] References Cited

U.S. PATENT DOCUMENTS

| | | | |
|---|---|---|---|
| 3,803,140 | 4/1974 | Cook et al. | 556/401 |
| 3,948,964 | 4/1976 | Barfurth et al. | 556/401 |
| 4,644,074 | 2/1987 | Manis et al. | 556/401 |

FOREIGN PATENT DOCUMENTS

| | | |
|---|---|---|
| 0126908 | 2/1948 | Australia . |
| A1329555 | 8/1989 | European Pat. Off. . |
| 56-109230 | 8/1981 | Japan . |
| 62-177051 | 8/1987 | Japan . |

*Primary Examiner*—Joseph Paul Brust
*Assistant Examiner*—MarySusan H. Gabilan
*Attorney, Agent, or Firm*—Birch, Stewart, Kolasch & Birch

[57] ABSTRACT

N,O-bis(trimethylsilyl)acetamide is improved in thermal stability by adding about 0.01 to 5 mol % of a 2-mercaptobenzothiazole or a salt thereof thereto.

10 Claims, No Drawings

N,O-BIS(TRIMETHYLSILYL) ACETAMIDE STABILIZATION

This invention relates to a method for stabilizing N,O-bis(trimethylsilyl)acetamide for improving the thermal stability thereof.

BACKGROUND OF THE INVENTION

As is well known in the art, N,O-bis(trimethylsilyl)acetamide is a very useful compound which is used as a silylating agent in the synthesis of organic compounds, especially pharmaceutical compounds. This compound, however, can be used only under limited conditions because it lacks thermal stability and is susceptible to decomposition reaction as shown by the following scheme when heated to high temperature.

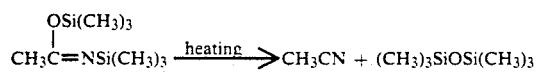

There exists a need for improving the thermal stability of N,O-bis(trimethylsilyl)acetamide.

SUMMARY OF THE INVENTION

The inventors have found that by adding a 2-mercaptobenzothiazole of the general formula (1):

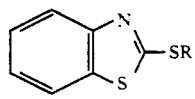
(1)

wherein R is selected from the group consisting of a hydrogen atom, alkylamino group, alkylthio group, alkylaminothio group, alkylammonium ion and alkali metal ion to highly active N,O-bis(trimethylsilyl)acetamide as a stabilizer, the thermal stability of N,O-bis(trimethylsilyl)acetamide can be improved to suppress its decomposition reaction when heated at high temperature. This enables the use of N,O-bis(trimethylsilyl)acetamide over a wider temperature range.

DETAILED DESCRIPTION OF THE INVENTION

In accordance with the present invention, N,O-bis(trimethylsilyl)acetamide is stabilized by adding a 2-mercaptobenzothiazole of formula (1) or a salt thereof thereto.

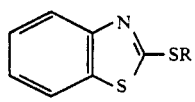
(1)

In formula (1), R is selected from the group consisting of a hydrogen atom, alkylamino group, alkylthio group, alkylaminothio group, alkylammonium ion and alkali metal ion. The alkyl chains in the alkylamino group, alkylthio group, alkylaminothio group, and alkylammonium ion preferably have 1 to 18 carbon atoms, more preferably 1 to 6 carbon atoms. The alkali metal ions include sodium ion, potassium ion, lithium ion, calcium ion, etc.

Several illustrative, non-limiting examples of the 2-mercaptobenzothiazole of formula (1) and salt thereof are given below as Compounds 1 to 7.

Compound 1
2-mercaptobenzothiazole

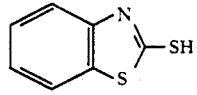

Compound 2
N-cyclohexyl-2-benzothiazolesulfenamide

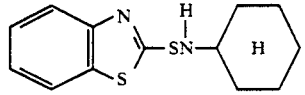

Compound 3
N-oxydiethylene-2-benzothiazolesulfenamide

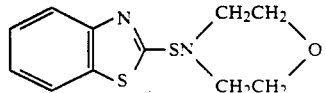

Compound 4
2-benzothiazoledisulfide

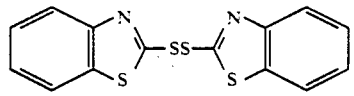

Compound 5
2-(4-morpholinyldithio)benzothiazole

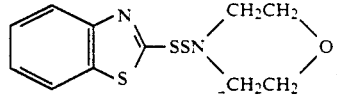

Compound 6
cyclohexylamine salt of 2-mercaptobenzothiazole

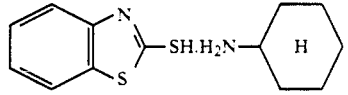

Compound 7
sodium salt of 2-mercaptobenzothiazole

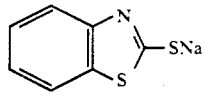

The 2-mercaptobenzothiazole or salt is preferably added in a amount of about 0.01 to 5 mol %, more preferably about 0.1 to 1 mol % based on the N,O-bis(trimethylsilyl)acetamide. Less than 0.01 mol % of the additive would sometimes fail to provide sufficient stabilization whereas more than 5 mol % of the additive gives rise to no problem, but might be rather economically undesired.

The method of the present invention improves the thermal stability of N,O-bis(trimethylsilyl)acetamide thereby suppressing the decomposition reaction thereof at high temperature. The present method is successful in maintaining N,O-bis(trimethylsilyl)acetamide intact, that is, a percent decomposition of 0% even after heating at 150° C. for 2 hours, for example. Accordingly, the present method spreads the applicable temperature range of N,O-bis(trimethylsilyl)acetamide.

EXAMPLE

Examples of the present invention are given below by way of illustration and not by way of limitation. Compounds 1 to 7 used in the examples are as previously defined.

EXAMPLE 1

A 50-ml four-necked flask equipped with a stirrer, condenser and thermometer was charged with 20.3 grams (0.1 mol) of N,O-bis(trimethylsilyl)acetamide and 0.835 grams (5 mol %) of Compound 1 as a stabilizer. With stirring, the contents were heated at 150° C. for two hours.

Analysis of the solution by gas chromatography showed that the percent decomposition of N,O-bis(-trimethylsilyl)acetamide was 0%.

The same heating test was carried out except that the amount of Compound 1 was reduced to 0.167 grams (1 mol %), resulting in a decomposition of 1%.

EXAMPLE 2

The procedure of Example 1 was repeated except that Compound 1 was replaced by Compounds 2 to 7 and their amount was varied between 0.01 mol % and 5 mol %. The results are shown in Table 1.

TABLE 1

| Compound Designation | Amount (mol %) | Decomposition of N,O-bis-(trimethylsilyl)acetamide % |
|---|---|---|
| 1 | 5 | 0 |
|   | 1 | 1 |
|   | 5 | 0 |
|   | 1 | 0 |
| 2 | 0.5 | 0 |
|   | 0.1 | 1 |
|   | 5 | 0 |
|   | .1 | 0 |
| 3 | 0.5 | 0 |
|   | 0.1 | 1 |
|   | 5 | 0 |
|   | 1 | 0 |
| 4 | 0.5 | 0 |
|   | 0.1 | 0 |
|   | 0.01 | 1 |
|   | 5 | 0 |
|   | 1 | 0 |
| 5 | 0.5 | 0 |
|   | 0.1 | 0 |
|   | 0.01 | 1 |
| 6 | 5 | 0 |
|   | 1 | 1 |
| 7 | 5 | 0 |
|   | 1 | 1 |

Table 1 shows that N,O-bis(trimethylsilyl)acetamide can be stabilized by adding any of Compounds 2 to 7.

COMPARATIVE EXAMPLE

A 50-ml four-necked flask equipped with a stirrer, condenser and thermometer was charged with 20.3 grams (0.1 mol) of N,O-bis(trimethylsilyl)acetamide. With stirring, the contents were heated at a fixed temperature between 50° C. and 150° C. for two hours.

The solutions were analyzed by gas chromatography to determine the percent decomposition of N,O-bis(-trimethylsilyl)acetamide. The results are shown in Table 2.

TABLE 2

| Heating temperature (°C.) | Decomposition of N,O-bis(trimethylsilyl)acetamide (%) |
|---|---|
| 50 | 0 |
| 60 | 0 |
| 80 | 1 |
| 100 | 5 |
| 120 | 95 |
| 150 | 100 |

As seen from Table 2, N,O-bis(trimethylsilyl)acetamide alone is thermally unstable.

Although some preferred embodiments have been described, many modifications and variations may be made thereto in the light of the above teachings. It is therefore to be understood that within the scope of the appended claims, the invention may be practiced otherwise than as specifically described.

We claim:

1. A method for stabilizing N,O-bis(trimethylsilyl)acetamide, comprising the step of
    adding to N,O-bis(trimethylsilyl)-acetamide a 2-mercaptobenzothiazole compound selected from the group consisting of a 2-mercaptobenzothiazole, N-cyclohexyl-2-benzothiazolesulfenamide, N-oxydiethylene-2-benzothiazolesulfenamide, 2-benzothiazoledisulfide, 2-(4-morpholinyldithio)benzothiazole; cyclohexylamine salt of 2-mercaptobenzothiazole and sodium salt of 2-mercaptobenzothiazole.

2. The method of claim 1 wherein the 2-mercaptobenzothiazole or salt is added in an amount of about 0.01 to 5 mol % based on the N,O-bis(trimethylsilyl)acetamide.

3. The method of claim 1, wherein the 2-mercaptobenzothiazole compound is added in an amount of about 0.1 to 1 mol % based on the N,O-bis(trimethylsilyl)-acetamide.

4. The method of claim 1, wherein the 2-mercaptobenzothiazole compound is 2-mercaptobenzothiazole.

5. The method of claim 1, wherein the 2-mercaptobenzothiazole compound is N-cyclohexyl-2-benzothiazolesulfenamide.

6. The method of claim 1, wherein the 2-mercaptobenzothiazole compound is N-oxydiethylene-2-benzothiazolesulfenamide.

7. The method of claim 1, wherein the 2-mercaptobenzothiazole compound is 2-benzothiazoledisulfide.

8. The method of claim 1, wherein the 2-mercaptobenzothiazole compound is 2-(4-morpholinyldithio)-benzothiazole.

9. The method of claim 1, wherein the 2-mercaptobenzothiazole compound is cyclohexylamine salt of 2-mercaptobenzothiazole.

10. The method of claim 1, wherein the 2-mercaptobenzothiazole compound is sodium salt of 2-mercaptobenzothiazole.

* * * * *